United States Patent [19]

Stokes

[11] Plant 4,805

[45] Jan. 19, 1982

[54] *CROSSANDRA INFUNDIBULIFORMIS* "DIANE"

[76] Inventor: Brian T. Stokes, Rte. 2, Box 11C, Vass, N.C. 28394

[21] Appl. No.: 142,575

[22] Filed: Apr. 18, 1980

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Cushman, Darby & Cushman

[57] ABSTRACT

A new and distinct cultivar of *Crossandra infundibuliformis* to be known as "Diane", the new cultivar being principally distinguished from the commonly cultivated variety by its larger sized and more broadly shaped leaves, its more robust and compact habit of growth and its flowers whose color is a darker, richer shade of salmon orange and whose petals are more rounded and larger in size than those of the commonly cultivated variety.

3 Drawing Figures

BACKGROUND AND SUMMARY OF THE INVENTION

The present invention relates to a new and distinct cultivar of *Crossandra infundibuliformis* which was discovered by me in the greenhouse of Green World in Red Springs, N.C. and which has been given the name "Diane".

At the time of discovery of the present invention, my attention was drawn to a particular plant grown from seed by myself which was quite different from the other crossandra seedlings by virtue of its rounded, thicker leaves and a more robust habit of growth. As this distinctively different plant grew to blooming size, I then noticed that it also produced flowers which were strikingly distinctive from those of the other crossandra plants, the flowers of "Diane" having noticeably larger and also more rounded petals and a distinctive color which was a darker, richer shade of salmon orange than that of the common variety. The flowers also exhibited noticeably larger yellow eye spots on the petals.

When I first began to asexually reproduce this plant, however, I noticed that as many times as not the new variety reverted to the older form. This is referred to in scientific terms as a mericlinal chimera. It took approximately two years of repeatedly taking cuttings from the original "Diane" before I was able to obtain a stable form of the new variety. Since the first stable form was obtained, I have successfully asexually propagated approximately 15 generations of "Diane" all of which have shown the aforementioned distinctive features.

The success in stabilizing the new form indicates the characteristics and distinctions are fixed and established and come through succeeding propagations.

DRAWINGS

The accompanying color photographic reproductions show typical speciments of my new cultivar "Diane", wherein.

DETAILED DESCRIPTION OF THE INVENTION

Name: *Crossandra infundibuliformis* "Diane"

Parentage: A cultivar of *Crossandra infundibuliformis*

Figure 1:
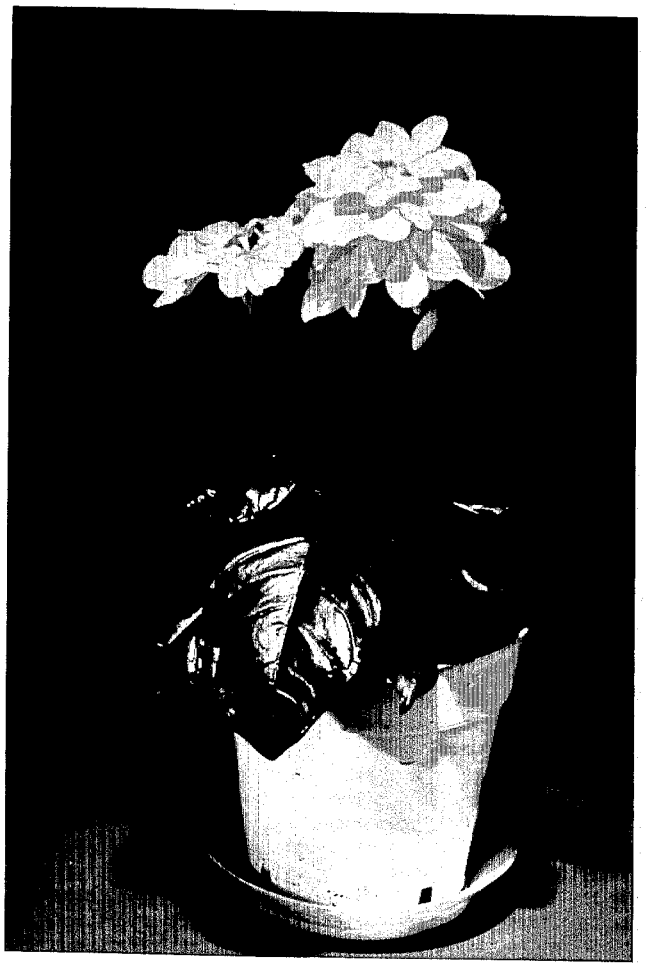
FIG. 1 is a view of a single, typical specimen of the new variety "Diane"
Figure 2:
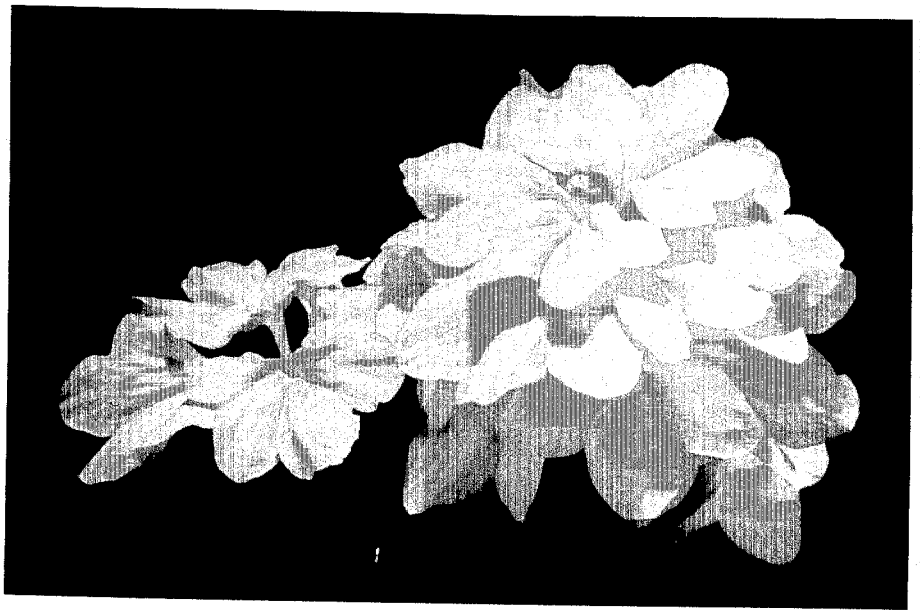
FIG. 2 is a close view of a typical flower of a typical specimen of the new cultivar "Diane"
Figure 3:
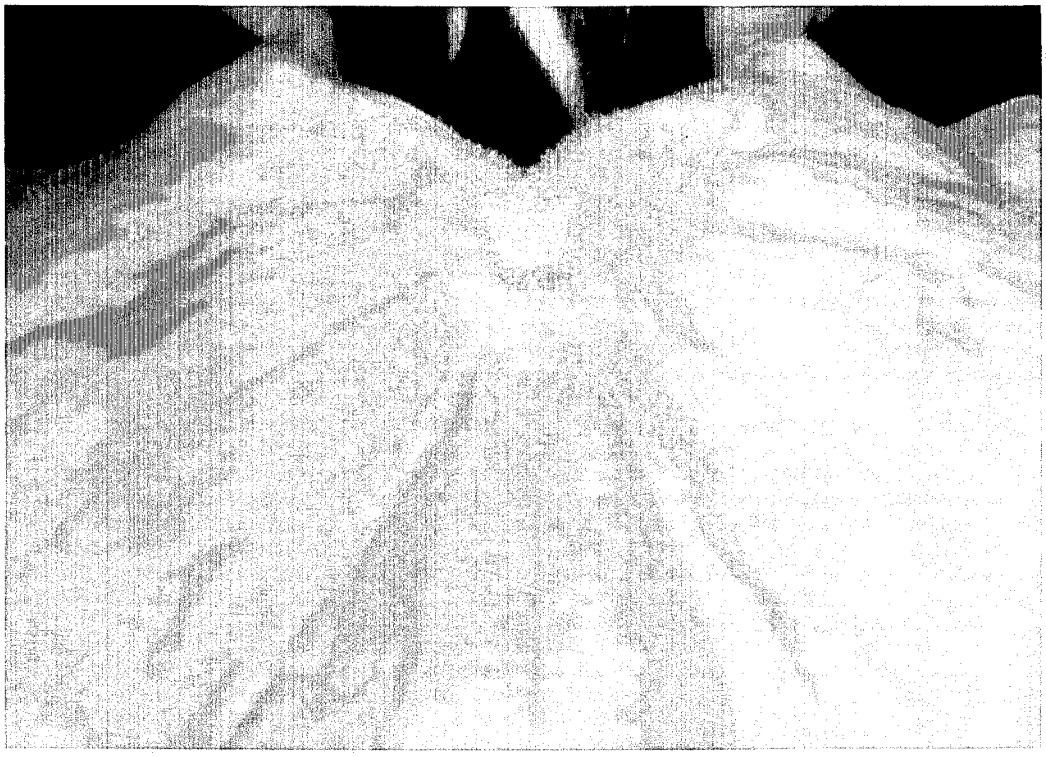
FIG. 3 is a close view of the eyespot of a typical flower of a typical specimen of the new cultivar "Diane".

Botanical classification: *Crossandra infundibuliformis* (L.) Nees cv. "Diane"; family Acanthaceae.

Plant: Perennial suffrutescent herb to subshrub, erect.

Leaves: Opposite, simple, decussate, exstipulate.

*Form.*—Oblong to ovate-oblong, apex acute to occasionally obtuse, base broadly cuneate and decurrent along petiole, margins entire, subundulate, upper surface dark green and more or less glossy, glabrous, lower surface green, glabrous; juvenile leaves oblong, blade sparsely pubescent on both surfaces, margin ciliolate.

*Size.*—Lamina 5–9 cm long, 3–6 cm wide; the ratio of the length/width is typically 1.4–1.8 (versus the ratio of 2–3 in the common variety).

*Veins.*—Campylodromous, impressed on the upper surface, conspicuously raised and pronounced on the lower surface; primary nerves of 7–11 pairs, strongly arcuate apically, anastomosing with the upper vein.

*Texture.*—Leathery and very smooth.

*Petioles.*—2–4 cm long, sunken adaxially between the decurrent blade; wings 1–2 mm wide.

Axillary buds: Ca. 1 mm long, scales densely appressed pubescent.

Inflorescence: Terminal on a long peduncle, erect, densely spicate.

*Peduncle.*—5–5.5 cm long (versus 6–7.5 cm long and ca 1.5 mm thick in the common variety), terete, 2–2.3 mm diam., minutely pubescent.

*Spike.*—Quadrangular, bracteated, conspicuously pubescent, approximately 10 cm long and 1.2 cm wide (versus 6–7.5 cm long in the common variety).

*Flowers.*—Bisexual, zygomorphic, commonly 4–8 expanded at one time on the inflorescence, subtended by large bracts (4–6 typically expanded at one time in the common variety).

*Bracts.*—Two, opposite, erect, green, prominently keeled, concave, elliptic-oblong, acute to short acuminate (acumen 1–2 mm), 16–19 mm long, 7–9 mm wide, densely pubescent; trichomes of abaxial surface of two types, (1) most of surface with dense appressed trichomes of ca 0.5 mm, and (2) trichomes clustered toward the margins and apex are 2–7 mm long, ascending-spreading, transparent, with several conspicuous septa.

*Bracteoles.*—Two, opposite, hidden by bracts and similar in pubescence to them, elliptic-linear, green toward apex and pale basally, acuminate (acumen 2–3 mm), 15–17 mm long, 2–3 mm wide.

Calyx: Of five connate parts, inconspicuous, hidden by the bracts, with a hard, short connate base and elongate, membraneous, free lobes; persistent in fruit.

*Tube.*—Very short, swollen, 1.5–2 mm long, glabrate.

*Lobes.*—Five, imbricate, unequal, membraneous, translucent, acuminate; outermost three lobes 11–13 mm long, 3–4 mm wide, weakly keeled; intermost two lobes 9–11 mm long, 2 mm wide, prominently keeled and subcomplicate.

*Pubescence.*—Dense, trichomes similar to those of the bracts.

Corolla: Of five connate parts divided into a tube and a limb.

*Tube.*—24–27 mm long versus 20–23 mm in the common variety), thin, terete, with a swollen basal segment (surrounding ovary), an erect middle segment (filaments borne near or at the apex), and an apical segment which is arcuate, outwardly curved; swollen basal segment 3–4 mm; erect middle section 8–10 mm; apical section 11–13 mm.

*Limb.*—24–29 mm long, 41–45 mm broad (versus 19–22 mm long, 27–30 mm broad in the common variety), dorsally split, flat, zygomorphic, with five lobes, the anterior lobe (middle lobe) being the largest and innermost before expansion, the posterior lobes (outermost lobes) being the smallest and outermost before expansion, lobes obtuse: anterior lobe 16–18 mm long, 12–14 mm wide, broadly obtuse; lateral lobes 11–13 mm long, 14–15 mm wide; posterior lobes (3) 5–7 mm long, (9) 11–13 mm wide (the lobes being generally longer, broader and more distinctly obtuse than those of the common variety).

*Pubescence.*—Dense on inner and outer surfaces of the tube, minute trichomes 0.2–0.5 mm long, spreading to reflexed, macrotrichomes scattered, spreading, 1–1.5 mm; trichomes on limb inconspicuous, moderate.

*Color.*—Salmon-orange Nasturtium Red 14/1 of British Color Council Horticultural Color Chart) with a yellow eye spot at the throat (eye color: Canary #3 of the Royal Horticultural Chart); eye 5 mm diameter (versus 3–4 mm diameter in the common variety).

Androecium: Stamens 4, didynamous, distinct, epipetalous, inserted 10–14 mm below the throat.

*Anters.*—Versatile, 1-loculate, villous along the margins.

*Filaments.*—Adnate with the corolla tube, free only apically; those of upper anther pair 0.5–1 mm long; those of lower anther pair 2–3 mm long.

Gynoecium: Pistil 1, of two fused carpels.

*Style.*—11–13 mm long, biforked apically (stigmatic area) ca 0.5 mm, slightly unequal.

*Ovary.*—Superior, 2-loculed, 3 mm long, 1 mm diam., terete-subtetragonous; ovules several.

Fruit: A 2-locular loculicidal capsule, oblong, subtetragonous, surface covered with minute scales and minutely pubescent toward apex; style more or less persisting.

*Seeds.*—Two per locule, imperfectly formed, oblong-orbicular, ca 1–1.2 mm×1 mm, lacking the testa of dense, fimbriately incised, coalescent scales.

What is claimed is:

1. A new and distinct cultivar of *Crossandra infundibuliformis,* substantially as described and illustrated, known by the cultivar name "Diane" and particularly characterized as having large and ovately-oblong shaped leaves, a robust habit of growth, and flowers having larger, more rounded petals and a color which is a darker, richer shade of salmon orange than found in the commonly cultivated variety.

* * * * *